US012150895B2

(12) United States Patent
Zhang et al.

(10) Patent No.: US 12,150,895 B2
(45) Date of Patent: Nov. 26, 2024

(54) SYSTEMS AND METHODS FOR AUTOMATED PHACOEMULSIFICATION

(71) Applicant: JOHNSON & JOHNSON SURGICAL VISION, INC., Irvine, CA (US)

(72) Inventors: Zheng Zhang, Laguna Beach, CA (US); Wayne Wong, Irvine, CA (US); Young Kim, Buena Park, CA (US); Abraham Hajishah, Irvine, CA (US); Summer Kraai, Tustin, CA (US); William Ade, Vista, CA (US); Dan Peters, Temecula, CA (US); Tamara Evans, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 44 days.

(21) Appl. No.: 17/447,289

(22) Filed: Sep. 10, 2021

(65) Prior Publication Data
US 2021/0401623 A1 Dec. 30, 2021

Related U.S. Application Data

(62) Division of application No. 16/151,261, filed on Oct. 3, 2018, now Pat. No. 11,141,313.

(51) Int. Cl.
*A61F 9/007* (2006.01)
*A61M 1/00* (2006.01)

(52) U.S. Cl.
CPC ........... *A61F 9/00745* (2013.01); *A61M 1/74* (2021.05); *A61M 1/77* (2021.05); *A61M 1/76* (2021.05);

(Continued)

(58) Field of Classification Search
CPC ................. A61F 9/00745; A61M 1/76; A61M 2205/3389; A61M 2210/0612
See application file for complete search history.

(56) References Cited

U.S. PATENT DOCUMENTS

| 5,160,317 A | 11/1992 | Costin |
| 5,279,547 A | 1/1994 | Costin |

(Continued)

FOREIGN PATENT DOCUMENTS

| DE | 3234621 A1 | 3/1984 |
| EP | 0741554 A1 | 11/1996 |

(Continued)

OTHER PUBLICATIONS

Co-pending U.S. Appl. No. 17/954,613, inventors Govari; Assaf et al., filed Sep. 28, 2022.

(Continued)

*Primary Examiner* — Nathan R Price
*Assistant Examiner* — John A Doubrava

(57) ABSTRACT

The present invention provides a system and a method for managing occlusions and reducing eye tissue damage during phacoemulsification surgery. More specifically, the present invention provides automated control of the application of ultrasonic energy to a partial or full occlusion of a surgical tool. The present invention measures the vacuum pressure and automatically adjusts the application of ultrasonic energy when the vacuum pressure indicates an occlusion or an occlusion break.

9 Claims, 2 Drawing Sheets

(52) U.S. Cl.
CPC ............... *A61M 2205/3389* (2013.01); *A61M 2210/0612* (2013.01)

(56) References Cited

U.S. PATENT DOCUMENTS

| | | | |
|---|---|---|---|
| 5,733,256 | A | 3/1998 | Costin |
| 5,836,990 | A | 11/1998 | Li |
| 6,690,280 | B2 | 2/2004 | Citrenbaum et al. |
| 8,246,580 | B2 | 8/2012 | Hopkins et al. |
| 8,414,605 | B2 | 4/2013 | Gordon et al. |
| 8,523,812 | B2 | 9/2013 | Boukhny et al. |
| 8,597,228 | B2 | 12/2013 | Pyles et al. |
| 9,144,517 | B2 | 9/2015 | Kuebler et al. |
| 9,282,989 | B2 | 3/2016 | Boukhny et al. |
| 9,545,335 | B2 | 1/2017 | Boukhny et al. |
| 9,707,127 | B2 | 7/2017 | Kadziauskas |
| 9,999,710 | B2 | 6/2018 | Ross et al. |
| 10,045,882 | B2 | 8/2018 | Balicki et al. |
| 10,070,988 | B2 | 9/2018 | McDonell et al. |
| 10,219,940 | B2 | 3/2019 | Raney et al. |
| 10,368,760 | B2 | 8/2019 | Hauck |
| 10,453,571 | B2 | 10/2019 | Teodorescu |
| 10,463,780 | B2 | 11/2019 | Mallough et al. |
| 10,596,033 | B2 | 3/2020 | Urich et al. |
| 10,940,039 | B2 | 3/2021 | Banko |
| 2004/0092800 | A1 | 5/2004 | MacKool |
| 2004/0193182 | A1 | 9/2004 | Yaguchi et al. |
| 2005/0209560 | A1 | 9/2005 | Boukhny et al. |
| 2005/0261628 | A1 | 11/2005 | Boukhny et al. |
| 2006/0079788 | A1 | 4/2006 | Anderson et al. |
| 2006/0100570 | A1* | 5/2006 | Urich .................. A61M 1/79 604/35 |
| 2006/0129140 | A1 | 6/2006 | Todd et al. |
| 2007/0073309 | A1 | 3/2007 | Kadziauskas et al. |
| 2007/0161972 | A1 | 7/2007 | Felberg et al. |
| 2008/0064935 | A1 | 3/2008 | Wong et al. |
| 2009/0118663 | A1 | 5/2009 | Rockley et al. |
| 2009/0182266 | A1 | 7/2009 | Gordon et al. |
| 2010/0069825 | A1 | 3/2010 | Raney |
| 2010/0118266 | A1 | 5/2010 | Nixon |
| 2010/0287127 | A1 | 11/2010 | Claus et al. |
| 2011/0015563 | A1* | 1/2011 | Boukhny ............ A61M 3/0208 604/22 |
| 2011/0313280 | A1 | 12/2011 | Govari et al. |
| 2012/0232466 | A1 | 9/2012 | Kuebler et al. |
| 2014/0018724 | A1 | 1/2014 | Staggs |
| 2014/0114296 | A1 | 4/2014 | Woodley et al. |
| 2014/0316254 | A1 | 10/2014 | Eversull et al. |
| 2014/0323953 | A1 | 10/2014 | Sorensen et al. |
| 2015/0073816 | A1 | 3/2015 | Ha et al. |
| 2015/0216726 | A1 | 8/2015 | Kadziauskas et al. |
| 2016/0175543 | A1 | 6/2016 | Frankhouser et al. |
| 2018/0028359 | A1 | 2/2018 | Gordon et al. |
| 2018/0092555 | A1 | 4/2018 | Script |
| 2018/0207330 | A1 | 7/2018 | Ovchinnikov et al. |
| 2018/0318131 | A1 | 11/2018 | Boukhny et al. |
| 2020/0309760 | A1 | 10/2020 | Durant |
| 2021/0196515 | A1 | 7/2021 | Urich |
| 2021/0361481 | A1 | 11/2021 | Gliner et al. |
| 2022/0008251 | A1 | 1/2022 | Govari et al. |
| 2022/0313489 | A1 | 10/2022 | Hajishah et al. |
| 2023/0043082 | A1 | 2/2023 | Govari et al. |
| 2023/0285189 | A1 | 9/2023 | Govari |
| 2023/0320897 | A1 | 10/2023 | Hajishah et al. |

FOREIGN PATENT DOCUMENTS

| | | |
|---|---|---|
| EP | 0956840 A2 | 11/1999 |
| EP | 1935383 A1 | 6/2008 |
| EP | 1 743 309 B1 * | 10/2011 |
| EP | 3448235 A2 | 3/2019 |
| JP | 4126304 B2 | 7/2008 |
| WO | 9211814 A1 | 7/1992 |
| WO | 2008016870 A2 | 2/2008 |
| WO | 2010014937 A1 | 2/2010 |
| WO | 2016122790 A1 | 8/2016 |
| WO | 2019069201 A1 | 4/2019 |
| WO | 2021119616 A1 | 6/2021 |

OTHER PUBLICATIONS

Co-pending U.S. Appl. No. 17/971,936, inventor Govari; Assaf, filed Oct. 24, 2022.
Co-pending U.S. Appl. No. 18/203,673, inventors Vadim; Gliner et al., filed May 31, 2023.
U.S. Appl. No. 16/727,100, titled "Phacoemulsification Apparatus," filed Dec. 26, 2019.
U.S. Appl. No. 17/357,587, titled "Accurate Irrigation Rate Measurment System and Method," filed Jun. 24, 2021.

* cited by examiner

SYSTEMS AND METHODS FOR AUTOMATED PHACOEMULSIFICATION

CROSS-REFERENCE TO RELATED APPLICATIONS

This application is a divisional of and claims priority to U.S. patent application Ser. No. 16/151,261, filed Oct. 3, 2018, which is incorporated herein by reference in its entirety.

BACKGROUND

Field of Invention

The present disclosure relates to the automated monitoring and control fluid inflow and outflow during a phacoemulsification procedure to promote a fluid balance within the eye that may bring particles and segments to the handpiece tip, detect occlusion by sensing vacuum, and discretely apply power to liquefy and aspirate material in a smooth, gentle manner that provides excellent particle hold and fluid flow.

Description of Related Art

During ophthalmic surgery, an ophthalmic surgical apparatus is used to perform surgical procedures in a patient's eye. An ophthalmic surgical apparatus typically includes a handheld medical implement or tool, such as a handpiece with a tip and/or sleeve, and operating controls for regulating settings or functions of the apparatus and tool. Operation of the tool requires control of various operating settings or functions based on the type of tool used. Such apparatuses typically include a control module, power supply, an irrigation source, one or more aspiration pumps, as well as associated electronic hardware and software for operating a multifunction handheld surgical tool. The handpiece may include a needle or tip which is ultrasonically driven once placed with the incision to, for example, emulsify the lens of the eye. In various surgical procedures, these components work together in order to, for example, emulsify eye tissue, irrigate the eye with a saline solution, and aspirate the emulsified lens from the eye.

Intraocular pressure (IOP) is the fluid pressure inside the anterior chamber of the eye. In a normal eye, intraocular pressure may vary depending on the time of day, activities of the patient, fluid intake, medications, etc. Intraocular pressure may be measured as static (a specific value) or dynamic (a range of values). As can be appreciated, the static IOP and dynamic IOP of a patient's eye can fluctuate greatly during an ophthalmic surgery procedure. It is well known that the IOP in an anterior chamber of the eye is required to be controlled and maintained during such surgical procedures in order to avoid damage to the patient's eye. For the correct function of the eye and its structure (e.g. shape) and to preserve sharp and undamaged vision, it is very important to keep the IOP in normal, physiological values.

An exemplary type of ophthalmic surgery is phacoemulsification. Phacoemulsification includes making a corneal and/or scleral incision and the insertion of a phacoemulsification handpiece that includes a needle or tip that is ultrasonically driven to emulsify, or liquefy, the lens. A phacoemulsification system typically includes a handpiece coupled to an irrigation source and an aspiration pump. The handpiece includes a distal tip that emits ultrasonic energy to emulsify a crystalline lens within the patient's eye. The handpiece includes one or more irrigation ports proximal to the distal tip and coupled to the irrigation source via an irrigation input line. The handpiece further includes an aspiration port at the distal tip that is coupled to the aspiration pump via an aspiration output line. Concomitantly with the emulsification, fluid from the irrigation source (which may be a bottle or bag of saline solution that is elevated above the patient's eye, to establish positive pressure by gravity, and/or with external pressure source) is irrigated into the eye via the irrigation line and the irrigation port(s). This fluid is directed to the crystalline lens in the patient's eye in order to maintain the anterior chamber and capsular bag and replenish the fluid aspirated away with the emulsified crystalline lens material. The irrigation fluid in the patient's eye and the crystalline lens material is aspirated or removed from the eye by the aspiration pump and line via the aspiration port.

Similarly, cataract surgery is a complex procedure performed by highly skilled surgeons using extremely complex and expensive equipment. The surgeon undergoes years of training to perfect their technique while using only a fraction of the system's capabilities and features. For example, cataract tissue, which may be denser, may be removed by aspiration. When the material has been emulsified or softened to the point where aspiration is sufficient to remove the material an occlusion break occurs. It is well known that excessive energy application after an occlusion break occurs, known as a post occlusion surge, could potentially damage the tissue. In practice, the surgeon may anticipate this occurrence and discontinue ultrasonic power to prevent any damage to the eye. If the occlusion break occurs faster than the surgeon can discontinue power, the surgeon may apply more power than needed. Studies have shown that the human reaction time is approximately 350 milliseconds (ms). That means the patient may be subjected to an additional 350 ms or more of ultrasonic energy every occlusion break.

For example, during segment removal, the surgeon may confront a multitude of decisions as he/she attempts to balance the inflow and outflow of fluid in the eye while trying to control the movement of material with the handpiece and deciding when to apply ultrasonic power. Additionally, lens material may create a blockage at the tip preventing fluid from being evacuated. This blockage can result in post-occlusion surge and lead to eye trauma. When faced with a potential post occlusion surge situation, the surgeon has to decide whether to preempt the surge by clearing the occlusion by applying power to knock the piece off the tip and having to reacquire the piece or discontinue the procedure by gradually (or quickly) releasing the foot pedal to change the pump speed and/or vacuum. Depending on the density of the material, length of occlusion, maximum aspiration rate, maximum vacuum and a wide variety of other factors, the occlusion may clear before the surgeon can take action. A disadvantage in releasing the footpedal is the fact that cataract lens material in the aspirating phacoemulsification handpiece may flow back into the eye chamber leading to a longer, less efficient cataract extraction.

Techniques to overcome post inclusion surge have been developed that include smaller or specialized tips that allow fluid to enter through a secondary port to allow continuous fluid flow. Alternatively, other techniques include modifying predefined vacuum or aspiration settings, adjusting vacuum manually during the procedure or automatically "on-the-fly", and releasing the foot pedal to discontinue aspiration. These techniques have had varying levels of success.

Thus, there exists a need for a simplified cataract extraction system where surgeons of many skill levels could safely and efficiently remove cataract lenses with a minimal amount of effort using a system that automates high portion the lens extraction procedure.

SUMMARY

A systems and methods for managing phacoemulsification surgery are disclosed. The present invention provides for ones of the irrigation inflow (which determines intraocular pressure), aspiration (speed in which the pump is pulling fluid from the eye), vacuum (which quantifies the quality of the occlusion) and power (which breaks up the particle or creates separation from the phaco tip) to be combined into a synergistic controlled system where lens material is drawn to the tip, aspirated and removed from the eye with limited user interaction. For example, such a system may be activated when a user simply positions the handpiece and depresses the foot pedal, thus activating the process.

The present invention provides a system for managing occlusions during phacoemulsification surgery, comprising a surgical console having at least one system bus communicatively connected to at least one computing processor capable of accessing at least one computing memory associated with the at least one computing processor, and at least one vacuum source associated with the surgical console for providing a vacuum pressure and at least one energy source associated with the surgical console for providing ultrasonic energy, wherein the ultrasonic energy is adjusted using the formula $f(x)=x+ax$ when exceeding a predetermined pressure threshold, and wherein $f(x)$ is a new current power, $x$ is a previous power, and $a$ is a factor or constant decimal less than 1.

A method for managing ultrasonic energy use during phacoemulsification surgery, the method comprising providing through a surgical instrument an ultrasonic energy and a vacuum pressure, receiving an indication of at least a partial increase in vacuum pressure in an aspiration line associated with a surgical handpiece, and adjusting the ultrasonic energy in accordance with the formula $f(x)=x+ax$ in responses to a received indication, wherein $f(x)$ is a new current power, $x$ is a previous power, and $a$ is a factor or constant decimal number less than 1. The power may be increased with every received indication until the maximum power setting is reached.

BRIEF DESCRIPTION OF THE DRAWINGS

The organization and manner of the structure and function of the disclosure, together with the further objects and advantages thereof, may be understood by reference to the following description taken in connection with the accompanying drawings, and in which.

DETAILED DESCRIPTION

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

Figure 1:
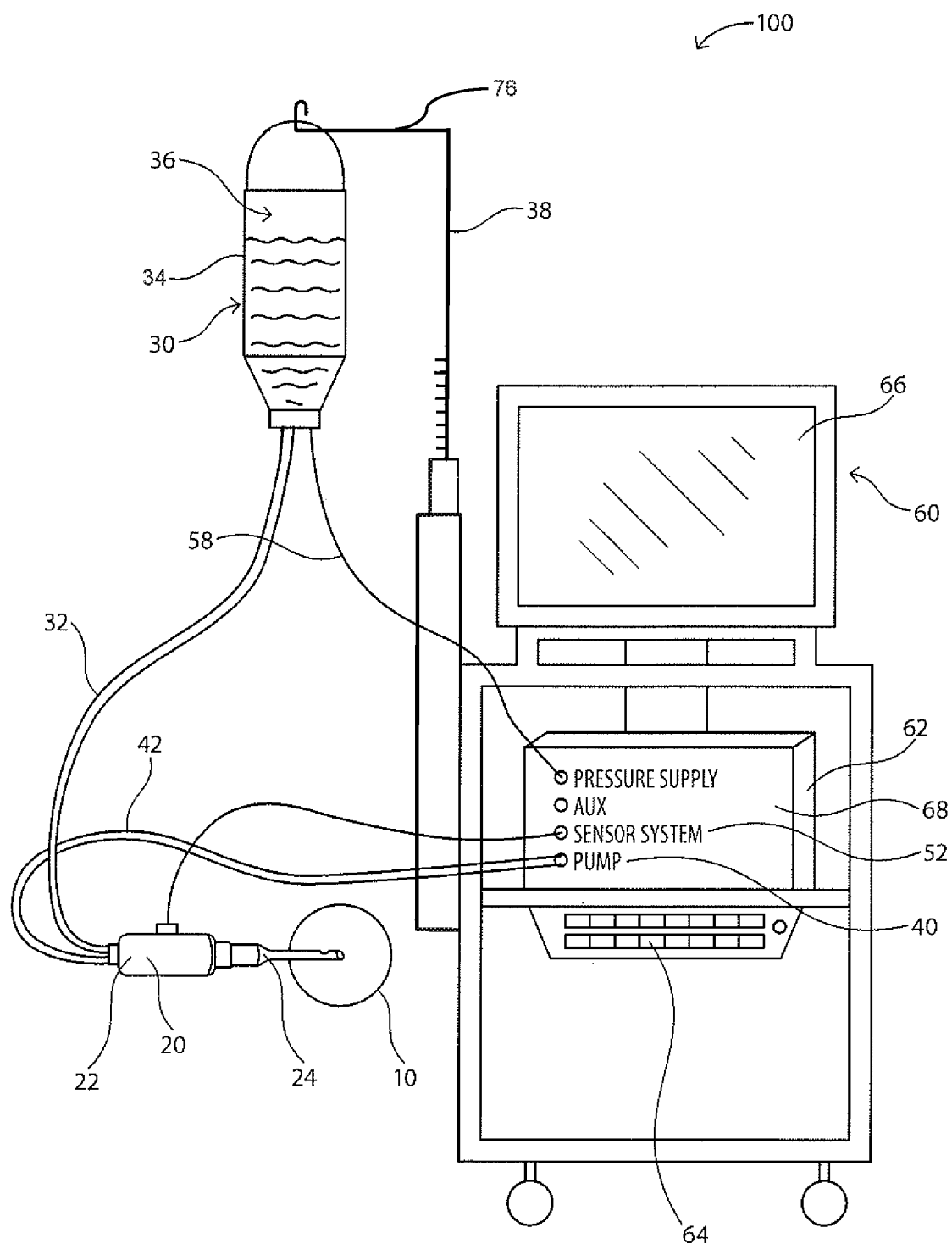
FIG. 1 illustrates a diagram of an exemplary phacoemulsification/diathermy/vitrectomy system in accordance with the present disclosure, the system including a control module to control various features of the system.
Figure 2:
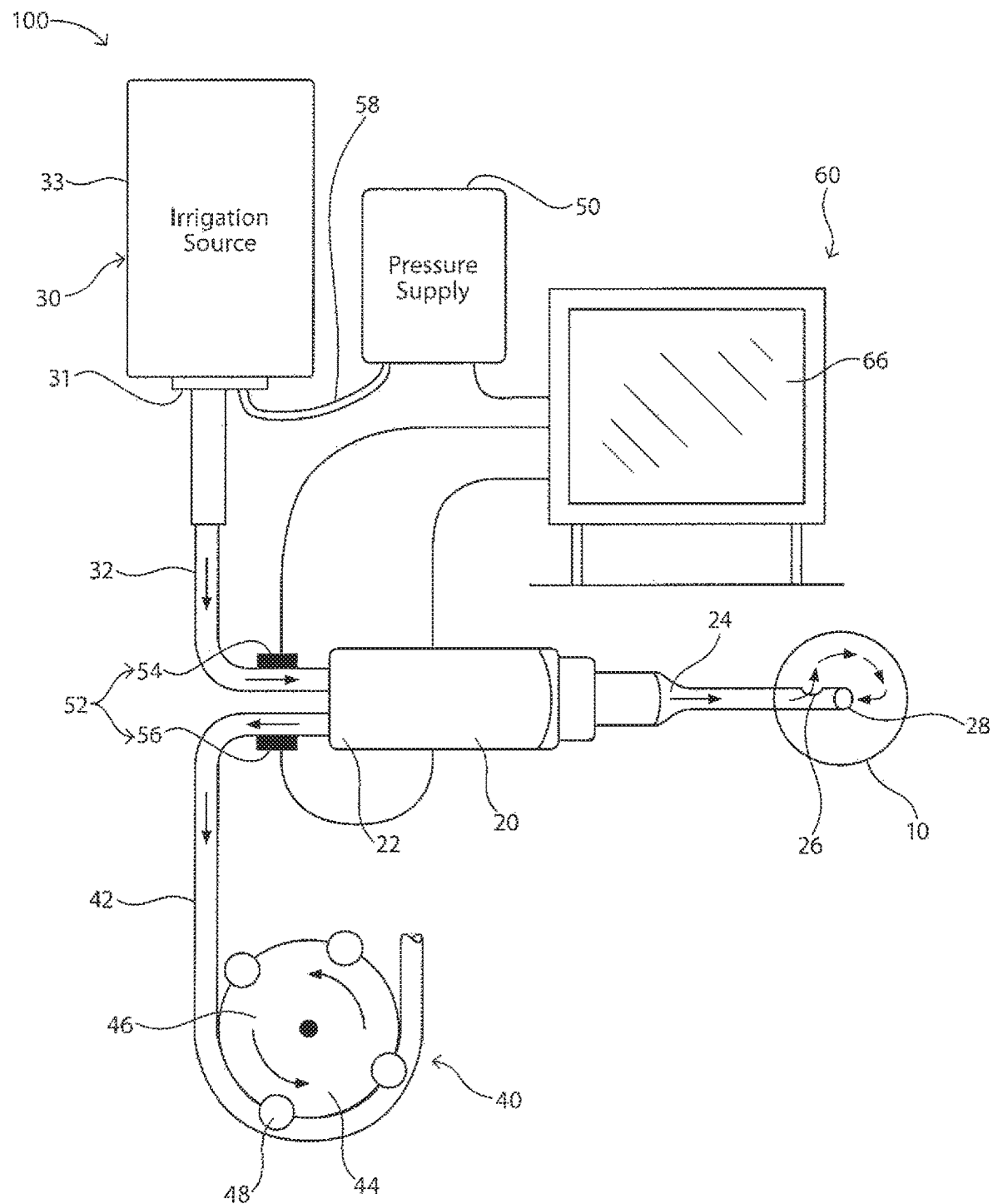
FIG. 2 illustrates an alternative phacoemulsification/diathermy/vitrectomy system and illustrated connected to various components of the system in order to determine characteristics or features of the components.

FIGS. 1 and 2 illustrate an exemplary phacoemulsification/diathermy/vitrectomy system 100. As illustrated, the system 100 includes, for example, a handpiece or wand 20, an irrigation source 30, an aspiration source 40, an optional pressure supply 50, and a control module 60. In illustrative embodiments, fluid is controllably directed through the system 100 in order to irrigate a patient's eye, illustrated representatively at 10, during an ocular surgical procedure. Various embodiments of the handpiece 20, irrigation source 30, aspiration source 40, optional pressure supply 50 and control module 60 are well known in the art and are embodied in this disclosure.

As illustrated in FIGS. 1 and 2, the irrigation source 30 is configured to supply a predetermined amount of fluid to the handpiece 20 for use during a surgical operation. Such fluid is supplied in order to, for example, stabilize or maintain a certain Intraocular Pressure (IOP) in the anterior chamber of the eye during surgery, as well as provide means for fluidly transporting any particles (e.g. lens particulates that are created during emulsification) out of the eye. Various aspects (e.g. the flow rate, pressure) of fluid flow into and out of the anterior chamber of the eye will typically affect the operations of the surgical procedure.

In illustrative embodiments, fluid may flow from the irrigation source 30 to the handpiece 20 via an irrigation line 32. The irrigation source 30 may be any type of irrigation source 30 that can create and control a constant fluid flow. In illustrative embodiments, the irrigation source is elevated to a predetermined height via a support 76 coupled with an extension arm 38. In illustrative embodiments, the irrigation source 30 may be configured to be an elevated drip bag 34 that supplies a steady state of fluid 36 to the irrigation line 32. Irrigation line 32 is coupled with proximal end 22 of handpiece 20. The pressure supply 50 may be coupled to the irrigation source 30 in order to maintain a constant pressure in the irrigation source 30 as fluid exits the irrigation source 30, as is known in the industry. Other embodiments of a uniform irrigation source are well known in the art.

During the surgical procedure, it is typically necessary to remove or aspirate fluid and other material from the eye. Accordingly, fluid may be aspirated from the patient's eye, illustrated representatively at 10, via the handpiece 20 to flow through an aspiration line 42 to the aspiration source 40. Aspiration line 42 is coupled with proximal end 22 of handpiece 20. The aspiration source 40 may be any type of aspiration source 40 that aspirates fluid and material from the eye. In illustrative embodiments, the aspiration source 40 may be configured to be a flow-based pump 44 (such as a peristaltic pump) or a vacuum-based pump (such as a Venturi pump) that are well known in the art. The aspiration source 40 may create a vacuum system to pump fluid and/or material out of the eye via the aspiration line 42. A sensor system 52 may be present to measure the pressure that the vacuum creates. Other embodiments of an aspiration source are well known in the art.

The irrigation port 26 is fluidly coupled to the irrigation line 32 to receive fluid flow from the irrigation source 30, and the aspiration port 28 is fluidly coupled to the aspiration line 42 to receive fluid and/or material flow from the eye. The pressure in the aspiration line may be measured by the sensor system 52. The handpiece 20 and the tip 24 may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well known in the art. Concomitantly with the emulsification, fluid from the irrigation source 30 is irrigated into the eye via the irrigation line 32 and the irrigation port 26. During and after such emulsification, the irrigation fluid and emulsified crystalline lens material are aspirated from the eye by the aspiration source 40 via the aspiration port 28 and the aspiration line 42. Other medical techniques for removing a crystalline lens also typically include irrigating the eye and aspirating lens parts and other liquids. Additionally, other procedures may include irrigating the eye and aspirating the irrigating fluid within concomitant destruction, alternation or removal of the lens.

The aspiration source 40 is configured to aspirate or remove fluid and other materials from the eye in a steady, uniform flow rate. Various means for steady, uniform aspiration are well known in the art. In illustrative embodiments, the aspiration source 40 may be a Venturi pump, a peristaltic pump, or a combined Venturi and peristaltic pump. In illustrative embodiments, and as shown in FIG. 2, a peristaltic pump 44 may be configured to include a rotating pump head 46 having rollers 48. The aspiration line 42 is configured to engage with the rotating pump head 46 as it rotates about an axis. As the pump head 46 rotates the rollers 48 press against the aspiration line 42 causing fluid to flow within the aspiration line 42 in a direction of the movement for the rollers 48. Accordingly, the pump 44 directly controls the volume or rate of fluid flow, and the rate of fluid flow can be easily adjusted by adjusting the rotational speed of the pump head 46. Other means of uniformly controlling fluid flow in an aspiration source 40 are well known in the art. When the aspiration source 40 includes a combined Venturi and peristaltic pump, the aspiration source 40 may be controlled to automatically switch between the two types of pumps or user controlled to switch between the two types of pumps.

In illustrative embodiments, the control module 60 is configured to monitor and control various components of the system 100. For instance, the control module 60 may monitor, control, and provide power to the pressure supply 50, the aspiration source 40, and/or the handpiece 20. The control module 60 may be in a variety of forms as known in the art. In illustrative embodiments, the control module 60 may include a microprocessor computer 62, a keyboard 64, and a display or screen 66, as illustrated in FIGS. 1 and 2. The microprocessor computer 62 may be operably connected to and control the various other elements of the system, while the keyboard 64 and display 66 permit a user to interact with and control the system components as well. In an embodiment a virtual keyboard on display 66 may be used instead of keyboard 64. A system bus 68 may be further provided to enable the various elements to be operable in communication with each other. The control module 60 may be powered by an energy source. One skilled in the art would appreciate that the energy source may be a power source—such as a 110 v plug—or conventional commercial power sources.

The screen 66 may display various measurements, criteria or settings of the system 100—such as the type of procedure, the phase of the procedure and duration of the phase, various parameters such as vacuum, flow rate, power, and values that may be input by the user, such as bottle height, sleeve size, tube length (irrigation and aspiration), tip size, vacuum rate. The screen 66 may be in the form of a graphical user interface (GUI) 70 associated with the control module 60 and utilizing a touchscreen interface, for example. The GUI 70 may allow a user to monitor the characteristics of the system 100 or select settings or criteria for various components of the system. For instance, the GUI 70 may permit a user to select or alter the maximum pressure being supplied by the pressure supply 50 to the irrigation source 30 via line 58. The user may further control the operation of the phase of the procedure, the units of measurement used by the system 100, or the height of the irrigation source 30, as discussed below. The GUI 70 may further allow for the calibration and priming of the pressure in the irrigation source 30.

In illustrative embodiments, the system 100 may include a sensor system 52 configured in a variety of ways or located in various locations. For example, the sensor system 52 may include at least a first sensor or strain gauge 54 located along the irrigation line 32 and a second sensor or strain gauge 56 located along the aspiration line 42, as illustrated in FIG. 2. Other locations for the sensors 54 and 56 are envisioned anywhere in the system 100, e.g. on the handpiece 20, and may be configured to determine a variety of variables that may be used to determine pressure measurements in the aspiration line, as discussed below. This information may be relayed from the sensor system 52 to the control module 60 to be used in the determination of the presence of an occlusion break. The sensor system 52 may also include sensors to detect other aspects of the components used in the system, e.g. type of pump used, type of sleeve used, gauge of needle tip (size), etc.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.), irrigation source height adjustment, linear control of settings, proportional control of settings, panel control of settings, and type (or "shape") of response.

The present invention may also monitor and control fluid inflow and outflow to generate a fluid balance within the eye that may bring particles and segments to the handpiece tip, detect occlusion by sensing vacuum, and discretely apply power to liquefy and aspirate material in a smooth, gentle manner that provides excellent holdability and followability. For example, extended periods of vacuum above a predetermined pressure threshold may indicate that the power being applied at the point of surgery is not effective or that the target lens material is denser than anticipated. In either of these situations, additional power or time may be needed. The present invention may provide for increasing the amount of power after a specified duration and may further provide subsequent power increases based on a time specification.

In an embodiment of the present invention, a surgeon may control the system of the present invention using, for example, a foot pedal associated with the system. There may be at least four "zones" in the foot pedal denoted by number for ease of explanation, with each zone being assigned a particular task and/or function. For example, a first zone may start at 0, representing no activity, a second zone may be "zone 1" and may engage and/or control irrigation functionality, "zone 2" may engage and/or control aspiration functionality, and "zone 3" may engage and/or control other aspects of the handpiece, such as the cutting tip. For example, when manually operating the foot pedal, a surgeon may press the pedal through positions 1 and 2 to control the fluidics of the system. Similarly, a surgeon my press the pedal to position 3 to apply ultrasonic power and then revert back to position 2 to discontinue power, for example.

The present invention provides a user control when power is to be activated and may engage an algorithm, such as a linear or binomial equation, to determine how much power gets applied while the user is in, for example, foot pedal position 3. By way of non-limiting example only, if no occlusion exists, zero to a minimal amount of power may be applied. If, for example, an occlusion exists, power may applied in two levels. A first power level may be provided to assist in acquiring the particle and may be provided for a defined initial period, such as, for example, 2 seconds. As the vacuum level increases, a second power level may be obtained and, for example, the system may discontinue the use of power given the expiration of the initial period and wait for a second designated period. This is to determine whether aspiration and vacuum alone is sufficient to remove the tissue. If the first period of time elapses and the occlusion remains, primary power may be applied to help emulsify the material. Additional power may be applied over a specific time period until the blockage is cleared. Once the blockage is cleared, power may be immediately reduced to the minimal power level. In an embodiment of the present invention. the user may remain in position 3 throughout this entire process while the amount or amplitude of power applied is determined automatically through the algorithm.

In an embodiment of the present invention, during a phacoemulsification procedure, the user may engage the foot pedal to initiate irrigation (foot pedal position 1) and activate aspiration (foot pedal position 2). Cataract lens material may be drawn to the tip and vacuum may be generated. The user may activate ultrasonic power (foot pedal position 3), for example, to aid in embedding the tip to acquire the material. Typically, the user will transition back into foot pedal position 2 for maintaining a hold over the material and then use a second instrument such as, for example, a chopper, to segment the material into smaller, more manageable pieces. This process of moving from foot pedal position 2, to foot pedal position 3, and back to foot pedal position 2, may be repeated until the user is satisfied with the quantity and size(s) of the material to be removed.

In an embodiment of the present invention, a user may engage foot pedal position 2 to attract a segment of loose tissue and attempt to remove it by aspiration alone. If the aspiration is not sufficient to remove the tissue, a complete blockage of the tip may occur creating at least a partial occlusion. The user may then engage foot pedal position 3 to activate ultrasonic power to emulsify the material to aid in aspiration. When, for example, the blockage has cleared or when the user determines the material has been emulsified satisfactorily, the user may revert back to foot pedal position 2, discontinuing ultrasonic power. This process is repeated until all lens material has been rem oved.

Furthermore, upon occlusion detection and applying an algorithm, such as described herein, to modulate the aspiration rates, increase and decrease the peristaltic pump speed to pulsate the pump, causing shearing forces on the particle. Ideally, these shearing forces will be sufficient to aspirate the tissue without the application of ultrasonic power. In an embodiment of the present invention, power may be applied sparingly and ideally, within a duty cycle that may maximize the reduction of thermal issues as power may only be applied if and when an occlusion is detected. If, for example, aspiration and vacuum are not sufficient to remove a blockage, ultrasonic power may be applied. Power may be applied manually, based on the user's judgment or via an automated algorithm (described herein) that detects the quality and length of the occlusion. In the proposed solution, ultrasonic power may be applied through a surgical console and handpiece combination which may allow for the application of power via a longitudinal (forwards and backwards) motion and/or via an elliptical pattern in a two-dimensional plane.

In an embodiment of the present invention, power control decisions may be based on monitoring vacuum level(s) after a user activates power via, for example, foot pedal position 3. By way of non-limiting example only, during manual nucleus removal, a surgeon may position the phacoemulsification needle in proximity to the tissue to be removed and draw it towards the tip of the needle. Once the portion of tissue is at least proximate to the needle tip, the surgeon may apply a small amount of power to embed the tip into the tissue to aid in segmenting the lens material. Using a combination of irrigation and aspiration may allow for pieces of tissue to brought to the needle tip to be removed. If a blockage occurs, the algorithm may determine when and how much power is to be applied.

In an embodiment of the proposed invention, if a vacuum rises above a predetermined threshold, for example, "threshold 1", an initial amount of power may be applied to help embed the tip into the target material. This may allow the surgeon to control the piece of material and may aid in the attempt to segment the target material. For example, a threshold may set based on a percentage of the maximum vacuum. For example, if the threshold is 75% and the maximum vacuum is preset to 400 mmHg, then the pressure threshold is 300 mmHg. Power may be applied based on a percentage of the maximum allowable power and may be incremented over time. For example, if the maximum allowable power is 40, the initial power applied is 40% of that maximum or 16. Power may be immediate or delayed based on user preference.

As discussed above, the present invention may provide for increasing the amount of power after a specified duration and may further provide subsequent power increases based on a time specification. In the example cited above, a power of 16 would be applied when the actual vacuum exceeds 300 mmHg. By way of further example, if the vacuum remains above the threshold after two seconds (user adjustable) additional power may applied. Power may be either linear or logarithmic and may be expressed using a formula such as x+ax, wherein x represents the previous power being applied and ax represents a percentage of the x power to be added to the then applied power. The formula may also be expressed as: $f(x)=x+ax$, where $f(x)$ is a function of x and is the new calculated power; where "a" is any factor or decimal constant number less than 1, e.g. 0.1, 0.2 or any other number less than 1. For example, power may be increased in a step-wise fashion, such as in/" increments of 20% of applied power, such that the next incremental power level to apply would be 19, then 23, 27, 32 and then 38—each occurring after a two second period of power application. In this example, it would take ten seconds of occlusion to reach the full maximum power of 40.

As would be understood by those skilled in the art, power may be discontinued after the vacuum level falls below the vacuum threshold. As an occlusion clears, the system may increase aspiration and attract other particles and the process may be repeated.

The previous description is provided to enable any person skilled in the art to make or use the disclosed embodiments. Various modifications to these embodiments will be readily apparent to those skilled in the art, and the generic principles defined herein may be applied to other embodiments without departing from the spirit or scope of the invention. Thus, the present disclosure is not intended to be limited to the embodiments shown herein but is to be accorded the widest scope consistent with the principles and novel features disclosed herein.

What is claimed is:

1. A method for managing ultrasonic energy use during phacoemulsification surgery, the method comprising:
   providing through a surgical instrument an ultrasonic energy and a vacuum pressure;
   receiving an indication of at least a partial increase in vacuum pressure in an aspiration line associated with a surgical handpiece; and
   applying ultrasonic energy through the surgical instrument by activating a switch to a select position, wherein while the switch is activated to the select position, an initial ultrasonic energy level is applied for a configured period of time, in response to the received indication and, while the indication continues above a threshold, automatically increasing the ultrasonic energy during each of a plurality of subsequent periods of a preconfigured time specification until a maximum ultrasonic energy level is reached, in accordance with the formula $f(x)=x+ax$,
   wherein $f(x)$ is a new power, x equals a previous power and a is a decimal constant less than 1.

2. The method of claim 1, wherein the switch comprises a foot pedal.

3. The method of claim 1, wherein the indication corresponds to a change in aspiration pressure where increasing pressure indicates at least a partial occlusion.

4. The method of claim 1, further comprising providing at least one sensor for measuring the vacuum pressure of the aspiration line.

5. The method of claim 1, wherein a=0.2.

6. The method of claim 1, wherein a=0.3.

7. The method of claim 1, wherein the increase in vacuum pressure is greater than 5 percent.

8. The method of claim 1, wherein the vacuum pressure is less than 300 mmHg.

9. The method of claim 1, wherein the vacuum pressure is less than 400 mmHg.

* * * * *